United States Patent [19]

Fischer

[11] Patent Number: 4,671,104

[45] Date of Patent: Jun. 9, 1987

[54] DEVICE FOR MEASURING THE PROPERTIES OF SOLID MATERIALS WHICH CAN BE DERIVED FROM THE BEHAVIOUR OF A PENETRATING BODY

[76] Inventor: Helmut Fischer, Industriestr. 21, 7032 Sindelfingen-Maichingen, Fed. Rep. of Germany

[21] Appl. No.: 606,922

[22] Filed: May 4, 1984

[30] Foreign Application Priority Data

Aug. 3, 1984 [DE] Fed. Rep. of Germany ....... 3408554

[51] Int. Cl.⁴ .............................................. G01N 3/42
[52] U.S. Cl. ...................................... 73/81; 73/150 R
[58] Field of Search .................... 73/81, 150 R, 865.3, 73/865.9, 818, 823

[56] References Cited

U.S. PATENT DOCUMENTS 4,094,188  6/1978  Bellouin et al. ......................... 73/81

FOREIGN PATENT DOCUMENTS 665245  5/1979  U.S.S.R. .................................. 73/81

OTHER PUBLICATIONS

Nishibori, M. et al., Ultra-Microhardness of . . . , Tester from Thin Solid Films, vol. 48, No. 3, Feb. 1, 1978, pp. 325-331.

*Primary Examiner*—Jerry W. Myracle

[57] ABSTRACT

An apparatus for nondestructive, absolute measurement of the properties of solid materials can be derived from the behavior of a body penetrating into the materials, having a guidance device which guides the penetrating body on the surface of the materials and an electrical evaluation circuit. The penetrating body is a probe-tip insert in a single-pole probe set on the material to measure the thickness of thin coatings in the range of several 1000 μm and less. An electrical drive is connected to the guidance device and presses the penetrating body with a specific but variable force onto the surface of the material, and a voltage output by the probe representing the coating thickness is passed on to an evaluating circuit.

22 Claims, 11 Drawing Figures

DEVICE FOR MEASURING THE PROPERTIES OF SOLID MATERIALS WHICH CAN BE DERIVED FROM THE BEHAVIOUR OF A PENETRATING BODY

The present invention relates to an apparatus for nondestructive, absolute measurement of the properties of solid materials which can be derived from the behaviour of a body penetrating into said materials having a guidance device which guides the penetrating body on the surface of said materials and an electrical evaluation circuit.

BACKGROUND OF THE INVENTION

Probably the best known example of the use of the behaviour of a penetrating body in a material to determine its properties is the measurement of material hardness. Here there exist a considerable number of methods, for example, Shore Hardness measurement, Vickers Hardness measurement, Rockwell Hardness measurement, Brinell Hardness measurement, Herbert's pendulum etc. In view of the fact that the surface layer is fully or partially destroyed, however, these methods cannot be used in a great many areas of application. For example, if the hardness of paint is to be measured, it may be the case that the paint layer is not completely penetrated. Despite this the paint is damaged and it is possible that a rust spot at the test point could form the nucleus of local corrosion, whereas the rest of the paint layer is still in order. For this reason, the finished object is not measured, rather a test specimen. The test specimen, however, is not the finished object.

There are also non-destructive methods for measuring the properties of solid materials which can be derived from their behaviour under penetration.

It is, for example, known that by placing an ultrasonic probe on a material the frequency mismatch can be measured. This method is very sensitive to the degree of coupling with the test object. In addition, it is not the hardness alone which is measured, because the measured value depends substantially on the modulus of elasticity of the material, the thickness of the coating and the shape of the object, in particular on the thickness. The method can only be used for comparative assessments and not for absolute measurements.

A further non-destructive method giving absolute measurements was described in the "Industrie Anzeiger" of Dec. 2, 1981 under the (transalted) title "Method for Testing the Case Hardness Distribution of Forgings". The device described is very expensive. It is also so large that the object must be brought to the device; the reverse is not possible. A force is applied inductively and the depth of penetration measured by optical displacement measurement. Due to the sensor system employed for measurement, it is not possible to safely determine the depth of penetration in the micrometer range. The method is designed for measurement of case hardness with typical penetration depths of 500 $\mu$m. Similar to the case of a micrometer screw gauge, the system requires a very rigid yoke. The depth of penetration at a given force is converted by a difficult-to-use nomogram, since the measured value is a complicated function of the force applied.

OBJECT AND STATEMENT OF THE INVENTION

The object of this invention is to indicate a device of the type specified in the introduction, which is inexpensive to manufacture, which is so small that it can be brought to the place of use, which measures nondestructively, which allows reproducible, absolute measurements, which can also actually measure the hardness of the topmost coating in the case of inhomogeneous materials, which leads to simple functional relationships, which has no exotic systems such as ultrasonic sensors, interference measurements or similar systems and which can also be used by unschooled personnel.

This object is achieved, according to the invention, wherein the penetrating body is a probe-tip insert in a single-pole probe set on the material to measure the thickness of thin coatings in the range of several 1000 $\mu$m and less, an electrical drive is connected to the guidance device and presses the penetrating body with a specific but variable force onto the surface of the material, and a voltage output by the probe representing the coating thickness is passed on to an evaluating circuit. The invention has the following advantages:

(a) The probes, which are already known, allow very precise measurements of coating thickness over a wide range of thicknesses. In view of the fact that very precise absolute measurements are possible, it is also possible to measure coating thickness differences to high precision. For example, for a coating thickness of 20 $\mu$m, a change in coating thickness of 0.05 $\mu$m is easily detected. Alternatively, in the range from 100 to 500 $\mu$m, a change of coating thickness of 0.1 $\mu$m is measured with ease. Such small changes in coating thickness can be generated by extremely low contact forces. To give an idea of the size of the necessary forces; these lie, for example, in the range of 0.05 to 1 N.

(b) These minimal forces do not destroy even the softest coating.

(c) In view of the fact that the necessary forces are very low, there is no danger that the device will bend under its own weight and it is possible to make it rigid enough for the purpose here described with very little expenditure of material.

(d) With such low forces, measurements are actually only made in the surface zone which in any case provides the most important testimony in most applications.

(e) With such small measurement areas, the measurements themselves leave no traces whatsoever.

(f) In view of the fact that high energies need not be applied, high energies need not be supplied also. It is therefore perfectly plausible to use the device with battery power.

(g) The measurement is practically displacement free, with all the resulting consequences.

(h) The device can be used to measure on very small and/or curved surfaces.

Probes which measure such thin coatings with high precison have been known for many years, and are described, for instance, in German Utility Pat. No. 72 43 915, German Utility Pat. No. 73 36 864, German Patent Disclosure No. 25 56 34 or the still to be published German Patent Application P 33 31 407.

Advantageously, the invention includes the following additional features.

The evaluation circuit receives a variable representative of the force expended. The features allow the properties to be measured to be the hardness of the material.

The evaluation circuit indicates the slope of the function d (coating thickness) versus F (force). The features allow the indication to be particularly simple because surprisingly enough the slope is constant since the function is linear.

The force is changed incrementally. The features allow a measurement point to be taken at every force increment and an average straight line to be laid through said points.

The increments are equal in size. The features allow the circuit for generating the force increments to be particularly simple and with widely separated measuring points the straight line to be laid with particular accuracy.

The electrical drive is provided by a rotary magnet. The features allow the use of a simple, commercially available electrical drive which operates displacement-free in continuous use, the moment of which and hence also the force of which is highly reproducible.

The electrical drive is provided by a linear motor. The features allow levers which are always necessary for generating force in the case of a rotary magnet to be dispensed with. Such linear motors could, for example, be of the type which are used in record players for generating the contact pressure at the stylus tip.

The guidance device is a lever which is rigidly connected to the output shaft of the rotary magnet and carries the probe perpendicular to the direction of rotation. The features allow intermediate gearing with its play to be dispensed with in view of the fact that the measurement is practically displacement free, the rotary motion of the rotary magnet leads to a quasilinear movement of the probe.

The lever has two arms and carries a counterweight on the face opposite the probe. The features allow the weight of the probe to be compensated for in a simple manner.

The probe is a single-pole probe. A two-pole probe could also be used, at least as far as the state-of-the-art is concerned. By usine a single-pole probe, however, the full or semi Kardan mounting which a two-pole probe would require together with its inevitable play can be dispensed with.

The penetrating body is a diamond. The features allow the characteristics of the penetrating body to remain constant even when very hard materials are to be measured.

The end surface of the penetrating body forms the frustrum of a cone with a solid angle of 120°+20°. The features allow the exist surface of the lines of force of the tubular mount holding the penetrating body to come near, but not too near, the surface of the material so that the lines of force of the probe do not have to travel very far.

The frustrum of the cone is rounded off to a crown with a radius of curvature of 0.1 to 0.3 mm. These values are very well-proven. Surprisingly enough, the slope of the straight line is only slightly dependent on the radius of curvature of the indentor. The difference between a radius of 0.15 and 0.2 mm is less that 5%. In practical measurements the depth of penetration is normally or the order of the rounded zone of the penetrating body tip.

The guidance device and the drive are for a portable instrument which is to be set on the material and has a weight of more than 300 grams. The features allow the weight of the device to be so great that it is not lifted by the force which is applied to the probe.

The instrument stands on three feet. The features allow static redundancy to be avoided.

One of the feet is a transistor. The features allow the temperature of the material to be included in the measurement inasmuch as the transistor is capable of acting as a heat sensor. The instrument has a heavy baseplate which has a cutout through which the probe passes. The features allow a protected arrangement of the probe on a rigid baseplate.

Electrical wires are fixed on one hand to the probe and on the other to a stationary point and are highly flexible. The features allow the restoring force of the wires to be considered negligible.

The wires have a fastening point which is located on the lever at the center of rotation of the rotary magnet. The features allow the stiffness of the wires to contribute to the force to the minimum degree possible so that inpractice they can be completely neglected.

The evaluation circuit receives a variable representative of time. The features allow the creep properties of the material to be measured, which is particularly important when the material is a plastic.

In this case, the force is to be held constant, however, any possible logarithm can be used. The features allow the indication to be simple because the measurement points lie on a straight line.

DESCRIPTION OF THE DRAWINGS

The invention is now described using preferred illustrative embodiments. The drawings show.

A metal plate 16 is rectangular, heavy and rigid. It stands on two grubscrews 17, 18 which are screwed into corresponding threaded bores in the plate 16 and which are located in the left and right hand rear corners as per FIG. 1. They lie symmetrical to a central plane 19. Also in this central plane 19 lies, as a third but non-adjustable foot, a transistor 21 which serves as a heat sensor and which can be used for measuring the temperature of a coating 22 which is deposited on a substrate 23. Vertical support columns 24 are screwed from below into the corn ers of the plate 16. A rigid, heavy metal cover plate 26 is screwed onto these from above. Together with the plate 16 and the support columns 24, this forms a very rigid, heavy, protective cage of sufficient weight. Symmetrical to the central plane 19, a rotary magnet assembly 27 is mounted on the rear of the plate 16 as per of FIG. 1. This can be bought freely on the market. It is rigidly fixed to plate 16 by means of an end-frame 28. The output shaft 29 of the rotary magnet assembly 27 which also lies in the central plane 19 passes through the end-frame 28. The output shaft 29 carries a lever 31, which can be best seen from the sectional drawing in FIG. 2, with a left arm 32 and a right arm 33. The lever 31 is metal, heavy and because of its broad construction absolutely rigid in the direction of rotation 34 for the pruposes under consideration. In order that the lever 31 follows the output shaft 29 absolutely proportionally, a lock washer with a large 36 contact area is provided on the rear of the lever 31 and is pressed flat against the central area of the lever 31 by a screw 37. Moreover, two grubscrews 38 are also provided which connect the lever 31 to the lock washer 36 as well.

Figure 1:
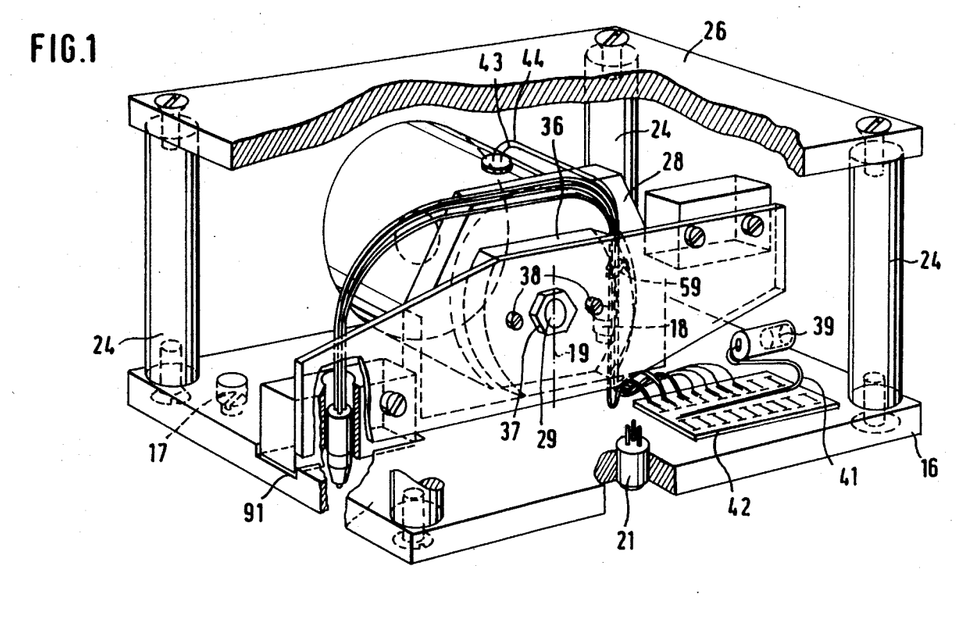
FIG. 1: a graphic illustration, partially sectioned, of a prototype version to a scale 1:1.4.
Figure 2:
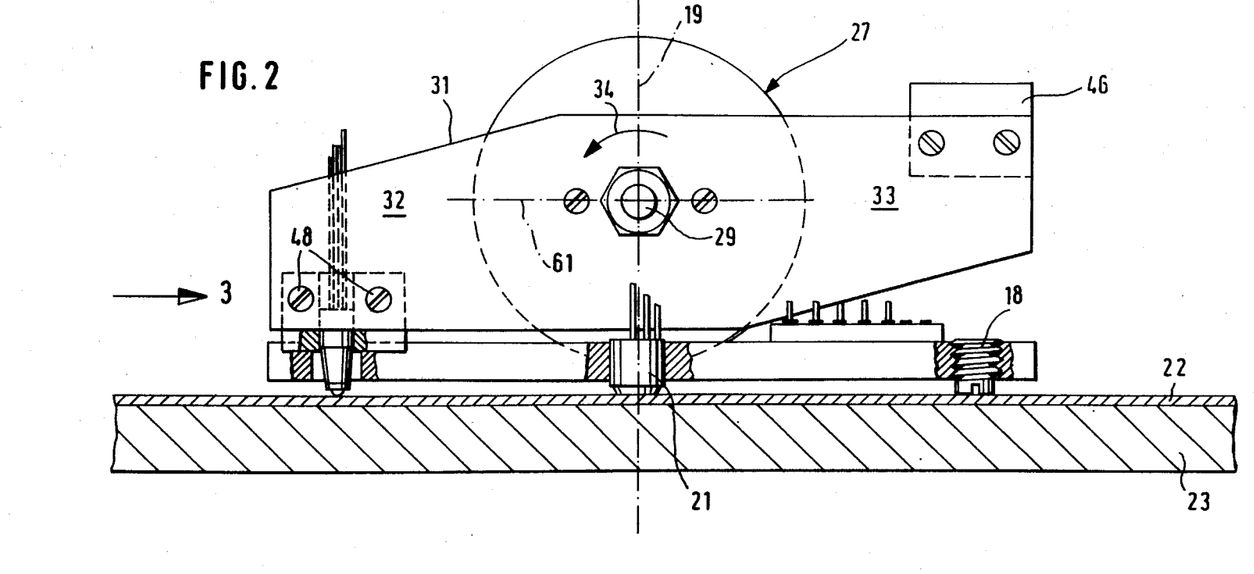
FIG. 2: the front view of FIG. 2, however, without support columns and cover plate, partially sectioned, to a scale 2:1.

In FIG. 1, top right, there is a multi-way socket 39, the wires of which run to a terminal board 42 that is mounted on plate 16 in front of the lever 31. Two wires 43, 44 run from the terminal board 42 to the rotary magnet assembly 27 without contacting the lever 31 or any of its associated parts. Such rotary magnet assemblies are designed to give precise, reproducible torques to the output shaft 29, insofar as the current in the wires 43, 44 has a particular value. The rotary magnet assembly 27 can be continuously operated without damage even when output shaft 29 is prevented from turning.

The right arm 33 carries a counterweight 45 which compensates for the weight of the probe assembly 47. The latter comprises a heavy metal block 49 which is screwed onto the rear of the left arm 32 by two screws 48. This has a through-bore 51 parallel to the central plane 19 which runs along a central axis 52. In the measuring position the central axis 52 stands perpendicular to the coating 22 and parallel to the central plane 19. Coaxial to the central axis 52 is the actual probe 53 which is cemented into the through-bore 51 by adhesive 54. Three highly flexible wires 56, 57, 58 leave the top of the through-bore 51, are bent as per FIG. 1, are fixed by a clip 59 at the intersection between the central plane 19 and the lever arm plane 61 and run from there to the terminal board 42. The probe 53 is cemented—using adhesive 54—rigidly over a wide contact area in part of the housing shaped as a retaining ring 62. The lower part of the retaining ring 62 forms a cone 63 which ends in a collar 64. A through-bore 66 coaxial to the central axis 52 passes through the retaining ring 62, cone 63 and collar 64. To the right a channel 67 for wires 56, 57, 58 leads upwards as per FIG. 5.

The through-bore 66 extends downwards into a coaxial, circular-cylindrical pot-core bore 68 (Fig.5), in which the shell 69 of a pot-core 71 is located. As per FIG. 5, the pot-core 71 has a coaxial thrust-washer 72 which is held by the through-bore 66. The pot-core 71 has a circular-cylindrical cylinder 73 coaxial to the central axis 52, the front face 74 of which stands proud of the bottom face 76 of the shell 69. The upper half of the space between the shell 69 and the cylinder 73 contains a primary coil 77. This is excited via wires 56 and 57 by a constant alternating current. A secondary coil 78, the bottom surface of which lies adjacent to the bottom face 76, is to be found below the primary coil 77. This is connected to wires 57, 58 which are connected to an indicator circuit 79. If the coating 22 is electrically non-conducting and the substrate 23 is non-magnetic the coil is excited with an alternating current of 500 kHz.

Figure 5:
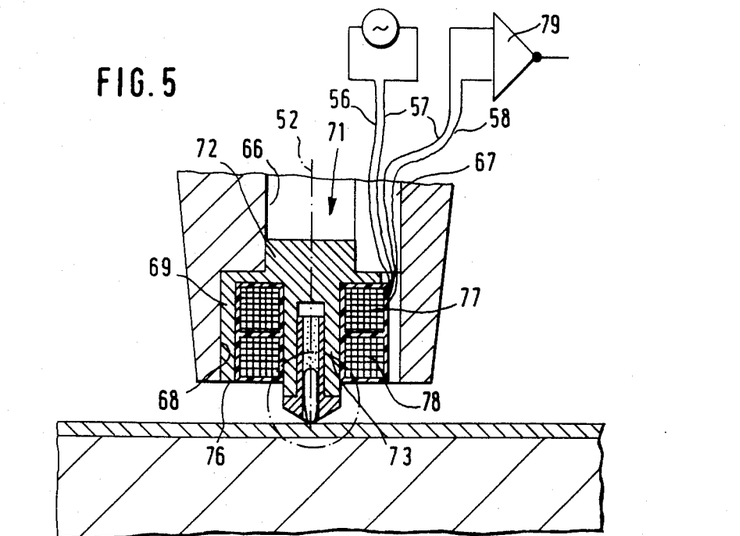
FIG. 5: an enlarged sectional view taken from FIG. 3 in the lower region of the probe at 13× magnification.

If the coating 22 is non-magnetic and the substrate 23 magnetic, the coil is excited with a low frequency alternating current of about 200 Hz. Depending on the application, the pot-core 71 can be made of soft iron or ferrite.

The cylinder 73 has a circular-cylindrical blind hole 81 which faces downwards. This contains an axially fixed miniature tubular mount 82 with an external flange 83 at the bottom, which fits smuggly with its rear, circular shoulder 84 against the front face 84; has an external surface 84 which lies flush with the external surface of the cylinder 73 and which has a lower face 84 which subtends an angle of 120° about the central axis 52. A diamond 86 is mounted in the lower part of the tubular mount 82 by means of adhesive or solder 87 so that it sits coaxially and rigidly fixed. The lower face 88 of the diamond 86 forms a circular cone with a solid angle of 120° which is mounted flush with the lower face 84 as per FIG. 6. The tip of the lower face 88 is rounded off, to form a radial crown 89 with a radius of 0.2 mm.

In all respects except the details of the diamond 86 and the tubular mount 82, such probes 53 represent state-of-the-art technology.

Figure 3:
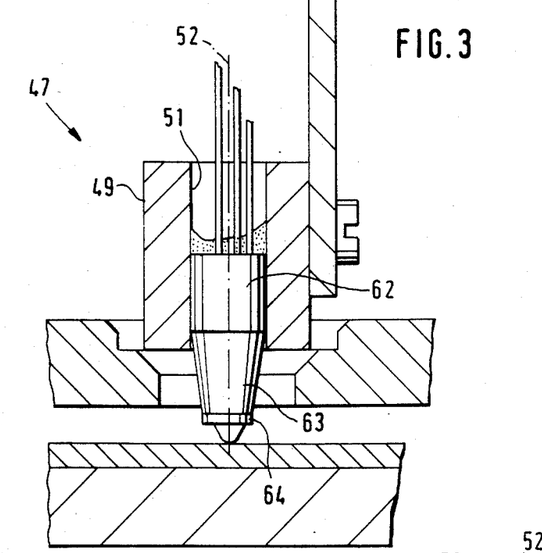
FIG. 3: a sectional view as per arrow 3 in FIG. 2 to a scale 3:1.
Figure 4:
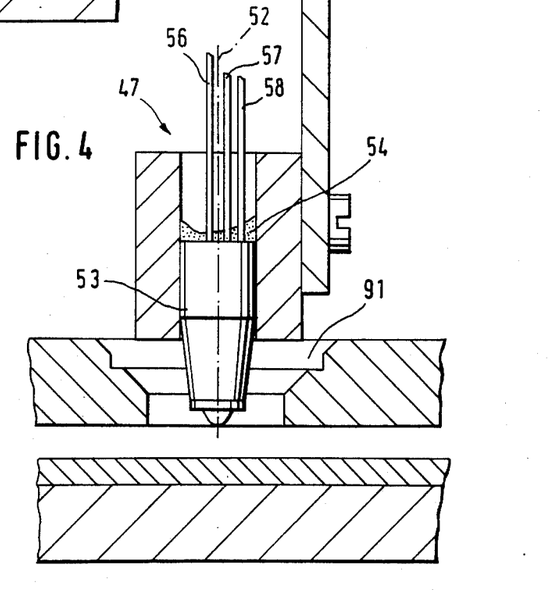
FIG. 4: a view as per FIG. 3 but with probe raised.

The plate 16 has a stepped cutout 91 below the left-hand end of the left arm 32. This allows the probe 53 to be brought into the operating position as per FIG. 3. When transported, the position shown in FIG. 4 is adopted, so that the diamond 86 is retracted upwards out of harm's way.

Figure 6:
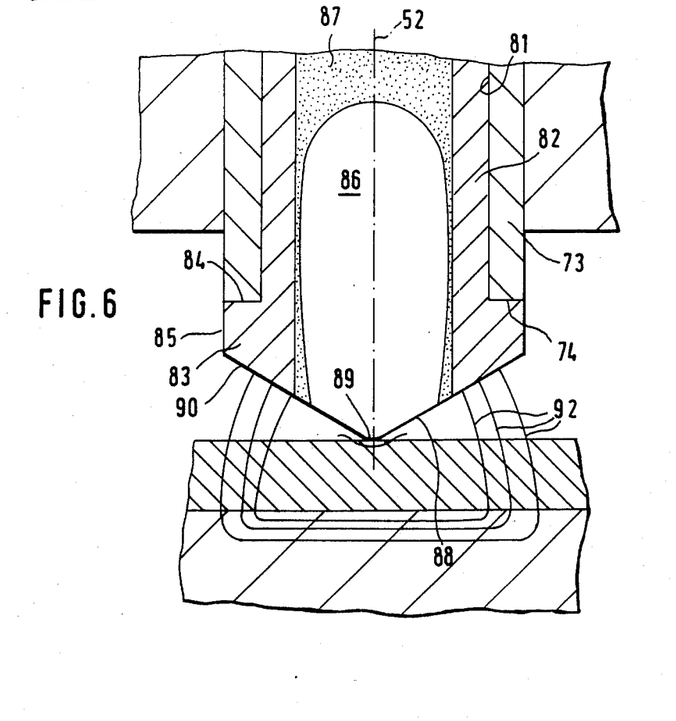
FIG. 6: a further enlargement of the dotted circle in FIG. 5 at 54× magnification.

In the operating position as per FIG. 6 the lines of force 92 run approximately as drawn, i.e., the penetration of lines of force at practically a single position, thus causing saturation due to their high concentration, has been avoided. The tubular mount 92 is made of a material with good magnetic conductivity such as Nickel-Iron.

Figure 11:
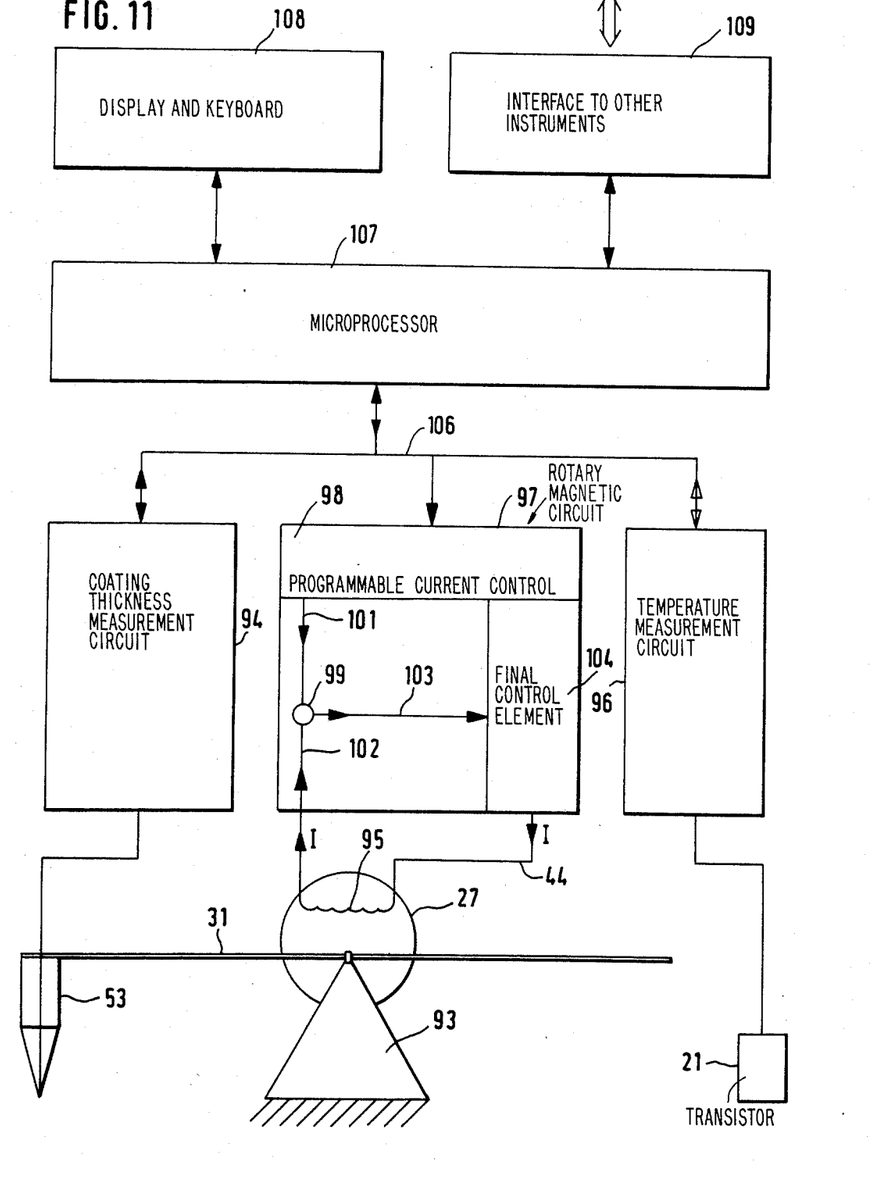
FIG. 11: a block diagram of the measurement system.

In the block diagram, FIG. 11, a solid base 93 is drawn which represents the plate 16 with support columns 24 and cover plate 26. The lever 31, the probe 53 and the transistor 21 ultilized as a temperature sensor can all be seen. Moreover the rotary magnet assembly 27 with its coil 95 is also present. A coating thickness measurement circuit 94 performs a normal coating thickness measurement with the probe 53. The temperature measurement circuit 96 performs a normal temperature measurement. The rotary magnet circuit 97 is provided with a programmable current control 98. This indicates the current flowing through the coil 95. The information is passed on to a nominal-actual comparitor 99 via a nominal current wire 101.

The nominal-actual comparitor 99 also receives the actual current via an actual current wire 102. The result of the comparison between nominal and actual current is passed on via a wire 103 to a final control element 104 which sets the correct current on wire 44.

A bus 106 leads to and from a microprocessor 107, whereby the direction of data flow is indicated by the arrows.

The microprocessor is provided with a display and keyboard 108. An interface 109 allows the system to be connected to other instruments.

A very important point concerning the control of the rotary magnet assembly is that the diamond 86—or any other penetrating body—is set down absolutely bounce-free on the coating. This is not because the diamond or any other test body could break, but rather that the test point is not pre-deformed by the kinetic energy associated with bouncing. In order to guarantee bounce-free setting down, a device such as that used to lower the stylus of a record player can be used, or the rotary magnet assembly 27 can be so controlled that the probe 53 is set down without bounce, etc.

Figure 7:
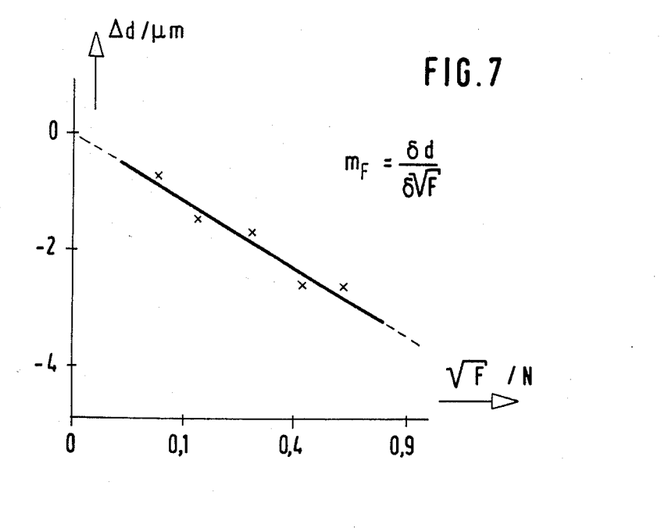
FIG. 7: a graph showing the hardness measurement.

If, for example, the hardness at the surface of coating 22 is to be measured, then after bounce-free setting down, a basic load must be applied, according to which the radial crown 89 indents the coating by a constant amount. This amount might be approximately 2%+0.1 μm. The force F is now increased and the coating thickness associated with each increment is measured simultaneously. In this way a non-linear relationship between change in coating thickness Δd and force F is obtained. If, as per FIG. 7, Δd is plotted as a function of $\sqrt{F}$, a linear function is found. The slope $m_F$, calculated as per FIG. 7, is a unambiguous measure of the hardness of the surface of the coating.

Figure 9:
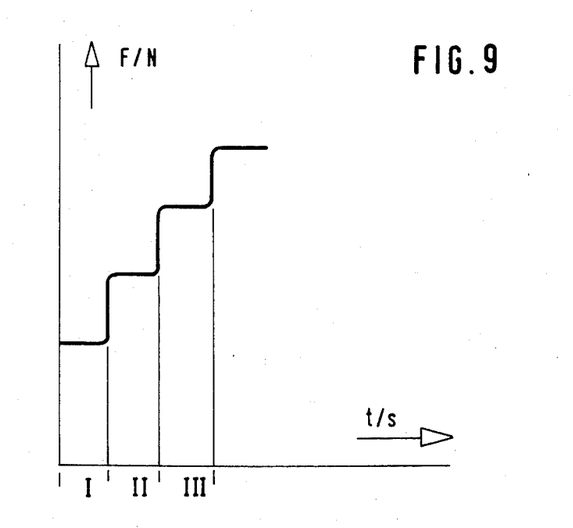
FIG. 9: a graph showing the force to be applied as a function of time.

The rotary magnet assembly 27 is excited with a stepped current as per FIG. 9, whereby the current is so chosen that a linear increase in force results. The time intervals I, II, III are identical and are typically 0.8 seconds long. The force develops with time as shown in FIG. 9.

Figure 10:
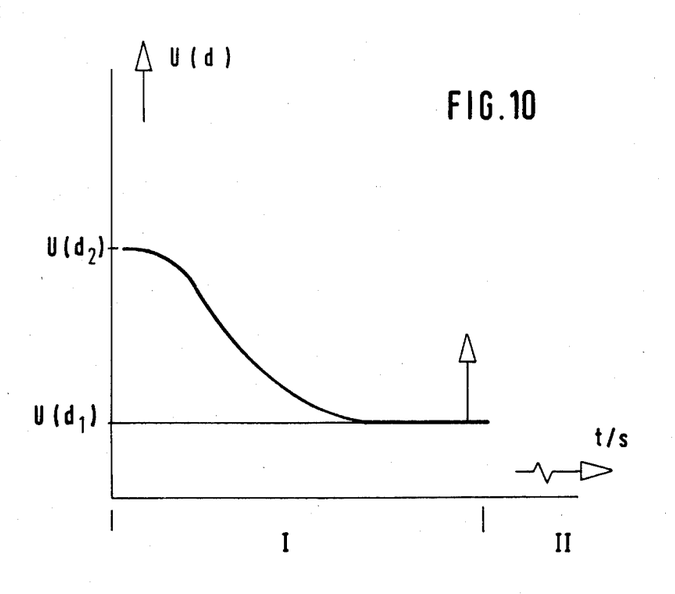
FIG. 10: the voltage given by the probe as a function of the time intervals as per FIG. 9.

FIG. 10 shows the voltage U (d) output by the probe 53 as a function of time during the interval I from FIG. 9. In view of the fact that the voltage U(d) output is a non-linear function of the coating thickness (d), the coating thickness circuit converts the change in coating thickness from the difference in the two values U(d1)−U(d2) such that measured value is directly proportional to be measured variable. Due to the moment of resistance generated when the diamond penetrates the surface of the coating 22 the voltage U(d) does not spontaneously follow the force F. For this reason the current increment I must be selected such that the voltage U(d) is practically constant when the voltage value is required. This point in time is indicated in FIG. 10 by the arrow pointing upwards. It can be seen that the acquisition is timed immediately before the start of period II. The same is true of periods II and III. The measured values are first stored, then processed further so that the transformed, linear relationship as per FIG. 7 results.

Figure 8:
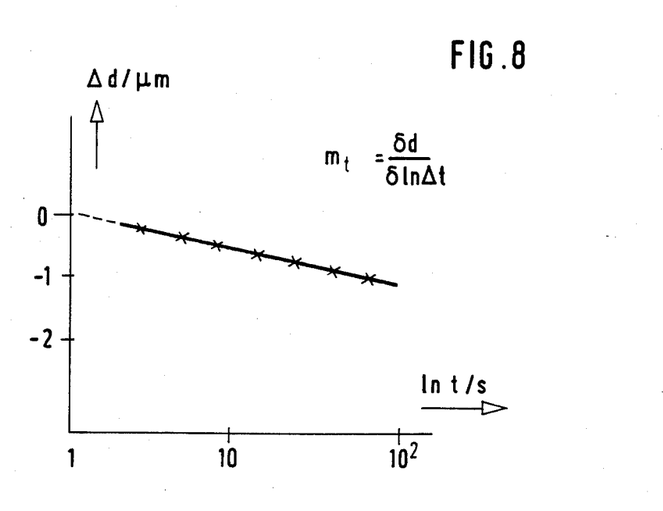
FIG. 8: a graph showing the creep behaviour.

If instead of the hardness, the creep behaviour of the coating 22 is to be determined, then the change in coating thickness Δd is acquired in equidistant logarithmic intervals. This information is processed and displayed at the display and keyboard unit 108. The slope of the line shown in FIG. 8 is a direct measure of the creep behaviour. The slope formula is given in FIG. 8.

Calibration values can be entered via the keyboard part 108 of the display, in as far as these are required for the various material property values.

The microprocessor 107 controls the rotary magnet assembly 27 with a constant current which is a measure for the specified torque. In view of the fact that the microprocessor 107 knows the distance of the radial crown 89 from the intersection of the central plane 19 with the lever arm plane 61, it can calculate the force F from these variables. Due to the constant current, temperature changes in the coil-resistor of the rotary magnet assembly 27 play no part in the measurement because the force increment is in fact constant.

The interface 109 can be used for various puposes. For example, a printer can be connected which ouputs characteristics of the kind shown in FIG. 7 and 8.

I claim:

1. Apparatus for nondestructive, absolute measurement of the properties of solid materials which can be derived from the behaviour of a body pressed onto said materials having a guidance device which guides the body on the surface of said materials and an electrical evaluation circuit, comprising the improvement wherein:
    (a) the body is a probe-tip insert in a known, voltage-generating probe in which a single pole is set on the material to measure the thickness of thin coatings in the range of several 1,000 μm and less, the known probe being of the type that presses without piercing the thin coatings,
    (b) an electrical drive is connected to the guidance device and presses the body with a specific predetermined but variable input force onto the surface of the material, and
    (c) means are provided for passing voltage outputs representing the coating thickness and the input force from the probe to the evaluation circuit.
2. Apparatus as claimed in claim 1, wherein the evaluation circuit receives a variable representation of the force exerted.
3. Apparatus as claimed in claim 2, wherein the evaluation circuit indicates the slope of the function d (coating thickness) versus F (force).
4. Apparatus as claimed in claim 2, wherein the force is changed incrementally.
5. Apparatus as claimed in claim 4 wherein the increments are equal in size.
6. Apparatus as claimed in claim 1, wherein the electrical drive is provided by a rotary magnet.
7. Apparatus as claimed in claim 6, wherein the guidance device is a lever which is rigidly connected to the output shaft of the rotary magnet and carries the probe perpendicular to the direction of rotation.
8. Apparatus as claimed in claim 7, wherein the lever has two arms and carries a counterweight on the face opposite the probe.
9. Apparatus as claimed in claim 1, wherein the electrical drive is provided by a linear motor.
10. Apparatus as claimed in claim 1, wherein the probe is a single-pole probe.
11. Apparatus as claimed in claim 1, wherein the body is a diamond.
12. Apparatus as claimed in one of claims 1 or 11, wherein the end surface of the body forms the frustrum of a cone with a solid angle of 120 degrees ±20 degrees.
13. Apparatus as claimed in claim 12, wherein the tip of the frustrum of the cone is rounded off to a crown with a radius of curvature of 0.1 to 0.3 mm.
14. Apparatus as claimed in claim 13, wherein the radius of curvature is 0.2 mm.
15. Apparatus as claimed in claim 1, wherein the probe, the guidance device and the drive are for a portable instrument which is to be set on the material and has a weight of more than 300 grams.
16. Apparatus as claimed in claim 15, wherein the instrument stands on three feet.
17. Apparatus as claimed in claim 16, wherein one of the feet is comprised of a transistor for measuring the temperature of the materials.
18. Apparatus as claimed in claim 15, wherein the instrument has a heavy baseplate which has a cutout through which the probe passes.
19. Apparatus as claimed in claim 1 comprising highly flexible electric wires connecting the probe to a stationary point on the apparatus.

20. Apparatus as claimed in claim 19, wherein the wires have a fastening point which is located on the guidance device at the center of rotation of the electrical drive.

21. Apparatus as claimed in claim 1, wherein the evaluation circuit receives a variable representative of time.

22. Apparatus as claimed in claim 21, wherein a variable representative of the logarithm of time is received.

* * * * *